United States Patent [19]
Yoon

[11] Patent Number: 5,728,112
[45] Date of Patent: Mar. 17, 1998

[54] COMBINED TISSUE CLAMPING AND SUTURING INSTRUMENT

[76] Inventor: InBae Yoon, 2101 Highland Ridge Dr., Phoenix, Md. 21131

[21] Appl. No.: 532,455

[22] Filed: Sep. 22, 1995

[51] Int. Cl.⁶ .................................................. A61B 7/04
[52] U.S. Cl. ........................ 606/144; 606/139; 606/146
[58] Field of Search .................................. 606/144, 145, 606/146, 148, 147, 139, 222, 223, 224, 225

[56] References Cited

U.S. PATENT DOCUMENTS

| | | |
|---|---|---|
| 373,372 | 11/1887 | King . |
| 786,000 | 3/1905 | Botkin . |
| 919,138 | 4/1909 | Drake et al. . |
| 1,037,864 | 9/1912 | Carlson et al. . |
| 1,066,317 | 7/1913 | Pirnat . |
| 1,449,087 | 3/1923 | Bugbee . |
| 1,635,066 | 7/1927 | Wells . |
| 1,815,725 | 7/1931 | Pilling et al. . |
| 1,822,330 | 9/1931 | Ainslie . |
| 1,856,721 | 5/1932 | Nagelmann . |
| 1,933,024 | 10/1933 | Nagelmann . |
| 2,213,830 | 9/1940 | Anastasi . |
| 2,396,180 | 3/1946 | Karle . |
| 2,414,746 | 1/1947 | Karle . |
| 2,611,366 | 9/1952 | Mull . |
| 2,646,045 | 7/1953 | Priestley . |
| 2,808,055 | 10/1957 | Thayer . |
| 2,959,172 | 11/1960 | Held . |
| 3,013,559 | 12/1961 | Thomas . |
| 3,090,386 | 5/1963 | Curtis . |
| 3,249,104 | 5/1966 | Hohnstein . |
| 3,349,772 | 10/1967 | Rygg ........................... 128/340 |
| 3,470,875 | 10/1969 | Johnson . |
| 3,638,653 | 2/1972 | Berry . |
| 3,840,017 | 10/1974 | Violante . |
| 3,842,840 | 10/1974 | Schweizer . |
| 3,901,244 | 8/1975 | Schweizer . |
| 3,946,740 | 3/1976 | Bassett . |
| 4,064,881 | 12/1977 | Meredith . |
| 4,164,225 | 8/1979 | Johnson et al. ............... 128/334 |
| 4,169,476 | 10/1979 | Hiltebrandt . |
| 4,224,947 | 9/1980 | Fukuda . |
| 4,312,337 | 1/1982 | Donohue . |
| 4,478,221 | 10/1984 | Heiss ............................ 128/334 |
| 4,493,323 | 1/1985 | Albright et al. . |
| 4,527,564 | 7/1985 | Eguchi et al. ................ 128/339 |
| 4,596,249 | 6/1986 | Freda et al. . |
| 4,602,635 | 7/1986 | Mulhollan et al. . |
| 4,621,640 | 11/1986 | Mulhollan et al. . |

(List continued on next page.)

FOREIGN PATENT DOCUMENTS

| | | | |
|---|---|---|---|
| 0535906 | 7/1993 | European Pat. Off. . | |
| 180125 | 7/1986 | Japan ............................ | 17/6 |

*Primary Examiner*—Michael Buiz
*Assistant Examiner*—Tina T. D. Pham

[57] ABSTRACT

A surgical instrument includes a pair of pivotally connected arms defining a pair of opposed jaws, a hollow suture needle mounted on a first of the jaws and provided with a slot, and a length of suture material extending through the hollow needle. The hollow needle has a first open end mounted on the first jaw and a second open end defining a tissue penetrating point, the first and second open ends being connected by the slot. A groove is preferably formed along an outer surface of the first jaw so that a portion of the suture material can be disposed within the groove and, when provided, the groove preferably communicates with the first open end of the hollow suture needle. The slot and groove each have a width to prevent the suture material from inadvertently falling out while permitting deliberate removal of the suture material via the slot or groove by application of force so that suturing of anatomical tissue can be performed with tissue held between jaws of the instrument. In a preferred embodiment, an opening is formed in the second jaw in opposed relation to the hollow suture needle such that, when the jaws are closed, the hollow suture needle will protrude from the opening and suture material disposed in the needle can be grasped and removed from the instrument without opening the jaws.

33 Claims, 6 Drawing Sheets

U.S. PATENT DOCUMENTS

| | | |
|---|---|---|
| 4,890,615 | 1/1990 | Caspari et al. . |
| 4,923,461 | 5/1990 | Caspari et al. . |
| 4,957,498 | 9/1990 | Caspari et al. . |
| 5,059,201 | 10/1991 | Asnis . |
| 5,100,421 | 3/1992 | Christoudias . |
| 5,181,919 | 1/1993 | Bergman et al. . |
| 5,254,126 | 10/1993 | Filipi et al. . |
| 5,304,184 | 4/1994 | Hathaway et al. . |
| 5,318,577 | 6/1994 | Li . |
| 5,320,632 | 6/1994 | Heidmueller . |
| 5,336,229 | 8/1994 | Noda . |
| 5,389,103 | 2/1995 | Melzer et al. . |
| 5,397,325 | 3/1995 | Della Badia et al. . |

COMBINED TISSUE CLAMPING AND SUTURING INSTRUMENT

BACKGROUND OF THE INVENTION

1. Field of the Invention

The present invention pertains to surgical instruments and, more particularly, to surgical instruments and methods for simultaneously clamping and suturing anatomical tissue during surgical procedures.

2. Discussion of the Prior Art

Suturing of bodily tissue, that is, the practice of using lengths of suture material to ligate or approximate tissue, is a time consuming part of most surgical procedures in both open surgery and endoscopic or closed surgery. By "open surgery" is meant surgery wherein the surgeon gains access to the surgical site by a relatively large incision, and by "endoscopic surgery" is meant minimally invasive surgery wherein the surgeon gains access to the surgical site via one or more portals through which endoscopes are introduced to view the surgical site and through which instruments, such as forceps, cutters, applicators and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue.

Conventional suturing with a suture needle and a length of suture material is often used in combination with clamping to control bleeding when tissue is to be cut or divided as part of the surgical procedure. Ordinarily, one or more clamps are applied to the tissue alongside the cutting line to control bleeding from the clamped portion of the tissue. Once clamped, the tissue is cut using a cutting instrument such as a scissors or knife, and a suture needle carrying a length of suture material is grasped by hand or with a needle holder and moved into the body. The needle is caused to penetrate and pass through the tissue adjacent the clamp until the point of the needle is observed to emerge from the opposite side of the tissue. The point of the needle is grasped as it emerges and is pulled away from the tissue to draw the suture material through the tissue. When a suitable length of suture material has been drawn through the tissue, the surgeon forms a ligature around the divided tissue adjacent the cut.

When suturing the anatomical tissue, it is important that the point of the needle be precisely aligned with the tip of the clamping instrument prior to being forced through the tissue. When surgery is to be performed in awkward and restricted spaces, it is difficult to position the needle adjacent the tip of the clamping instrument since there is little room for maneuvering instruments and a greater chance of visual obstruction. It is, therefore, desirable to avoid the use of multiple instruments for tissue clamping and suturing, particularly in certain relatively inaccessible anatomical spaces.

U.S. Pat. No. 2,213,830 to Anastasi discloses a suturing and ligating instrument having a pair of gripping levers pivotally connected with a needle operating lever, one of the gripping levers pivotally mounting a curved needle and the other gripping lever being bifurcated to receive the needle between branches of the bifurcation. A length of suture material is attached to the needle via an eye formed near the point of the needle and is disposed alongside the needle during operation of the instrument. The needle operating lever is biased away from the gripping lever carrying the needle such that, in a normally open condition, the needle operating lever pivots the needle outwardly of the gripping lever via a stop acting on an inner concave surface of the needle. In a closed condition, the needle operating lever pivots the needle through both gripping levers and any tissue held therebetween. The suture material is carried alongside the needle as it is swung through the tissue and, as a result of the added bulk, this type of instrument is likely to create a larger hole than the size of the needle or suture material with additional trauma to the tissue.

U.S. Pat. No. 3,470,875 to Johnson describes a surgical clamping and suturing instrument having pivotally interconnected arms with one or more apertures being formed at the outer end of one of the arms for receiving and gripping a needle and a capsule containing a suture with one or more needles connected thereto being removably mounted at the outer end of the opposed arm. Upon closing of the arms, the needles are transferred from the capsule to the receiving apertures, carrying a length of suture material with them. A disadvantage of this type of device is that the arms must be opened in order to grasp the length of suture material extending through the tissue; and, accordingly, it is not possible to tie a ligature or stitch while simultaneously releasing clamping pressure on the tissue.

U.S. Pat. No. 4,596,249 to Freda et al discloses an instrument for setting sutures having a pair of pivotally connected arms, one of the arms forming a jaw with a tissue piercing hook and the other arm forming a jaw with a notch or opening for receiving the hook. A length of suture material extends across the notch or opening in opposed relation to the tissue piercing hook and is caught by an inner concave surface of the hook when the hook penetrates through anatomical tissue and is subsequently withdrawn. The hook is generally triangular in shape with a broad base and a pointed or sharpened end, the size of the hook being sufficiently large to form a concave inner surface suitable for catching the suture material as it is withdrawn from the opening in the opposed jaw and, consequently, causing additional trauma to the tissue.

SUMMARY OF THE INVENTION

Accordingly, it is a primary object of the present invention to provide a combined tissue clamping and suturing instrument overcoming the above-mentioned disadvantages of the prior art.

Another object of the present invention is to permit various types of sutures to be formed without the need of having to use multiple tissue clamping and needle holding instruments.

A further object of the present invention is to facilitate accurate placement of a needle adjacent clamped anatomical tissue for suturing without the need of having to directly visually observe the needle.

An additional object of the present invention is to permit easy removal of a length of suture material from the needle of a combined tissue clamping and suturing instrument without opening the jaws of the instrument such that suturing can be performed substantially simultaneously with removal of the clamping pressure.

The present invention has another object in minimizing penetration resistance of a suture needle mounted on a jaw of a combined tissue clamping and suturing instrument in order to reduce tissue trauma.

Still another object of the present invention is to permit anatomical tissue to be clamped, cut and sutured without the need of having to use separate tissue clamping, needle holding and cutting instruments.

Yet a further object of the present invention is to facilitate placement of a suture immediately adjacent a cut edge of anatomical tissue in order to minimize the amount of tissue overhanging the suture.

The present invention is generally characterized in a surgical instrument including a pair of pivotally connected arms defining a pair of opposed jaws, a hollow suture needle mounted on a first of the jaws and provided with a slot, and a length of suture material extending through the hollow needle. The hollow needle has a first open end mounted on the first jaw and a second open end defining a tissue penetrating point, the first and second open ends being connected by the slot. A groove is preferably formed on an outer surface of the first jaw so that a portion of the suture material can be disposed within the groove and, when provided, the groove preferably communicates with the first open end of the hollow suture needle. The slot and groove each have a width to prevent the suture material from inadvertently falling out while permitting deliberate removal of the suture material via the slot or groove by application of force so that suturing of anatomical tissue can be performed with tissue held between jaws of the instrument. In a preferred embodiment, an opening is formed in the second jaw in opposed relation to the hollow suture needle such that, when the jaws are closed, the hollow suture needle will protrude from the opening and suture material disposed in the needle can be grasped and removed from the instrument.

Another aspect of the present invention is generally characterized in a surgical instrument including a pair of pivotally connected arms defining a pair of opposed jaws, a longitudinal cutting channel formed in a first of the jaws, a cutting member movable along the longitudinal cutting channel, a suture needle extending from the first jaw to a tissue penetrating point and a length of suture material attached to the suture needle near the tissue penetrating point.

A further aspect of the present invention is generally characterized in a surgical instrument including a pair of pivotally connected arms defining a pair of opposed jaws, a plurality of longitudinally spaced suture needles, each of the needles extending from a first one of the jaws to a tissue penetrating point, and plural lengths of suture material, each of the lengths being attached to one of the suture needles near a respective tissue penetrating point.

An additional aspect of the present invention is generally characterized in a surgical instrument including a pair of pivotally connected arms defining a pair of opposed jaws, a plurality of laterally spaced suture needles, each of the needles extending from a first one of the jaws to a tissue penetrating point, and plural lengths of suture material, each of the lengths being attached to one of the suture needles near a respective tissue penetrating point.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figures 1, 2, 5, 6, 7, 8:
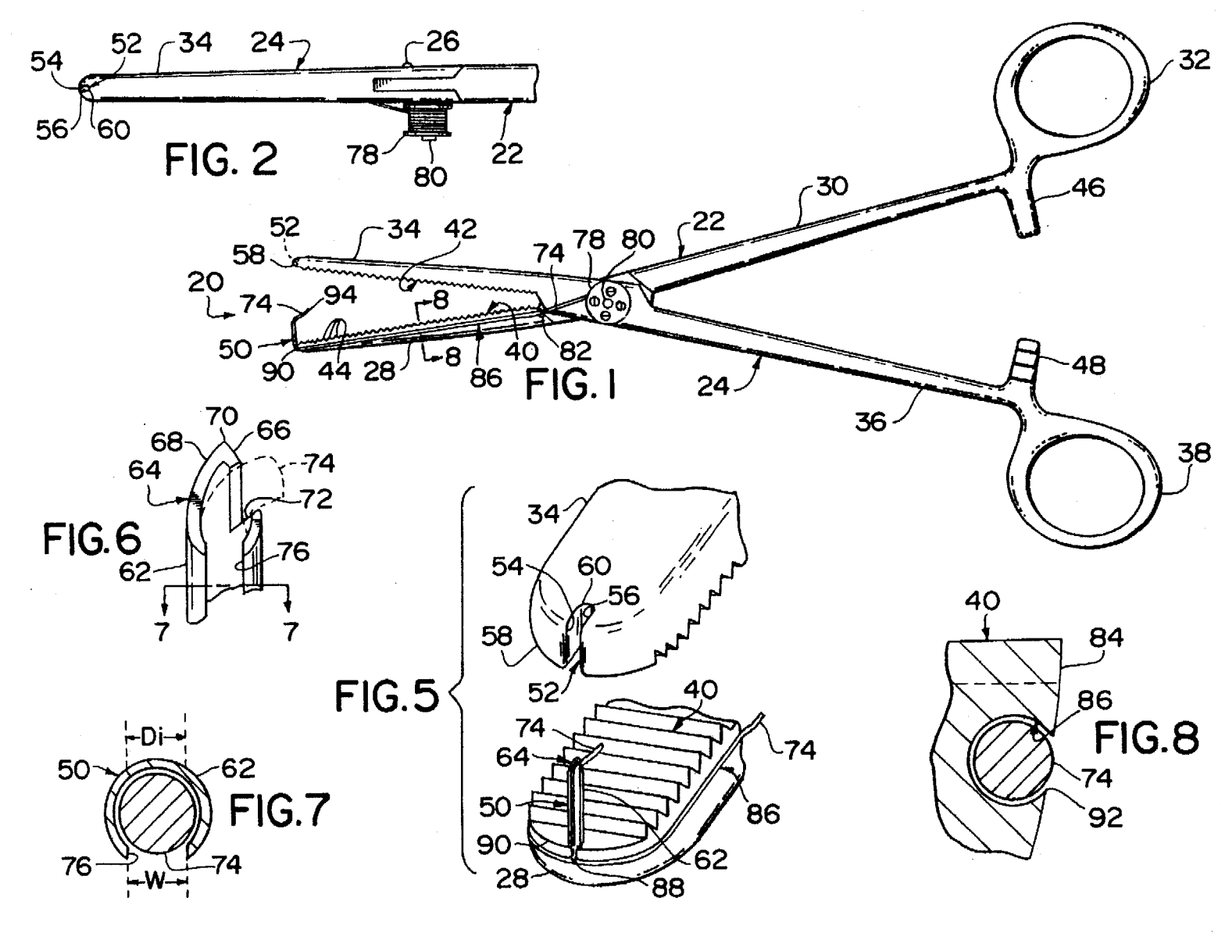
FIG. 1 is a side view, in elevation, of the surgical instrument of the present invention in an open position.
FIG. 2 is a fragmentary top view, in plan, of the surgical instrument of FIG. 1.
FIG. 5 is a fragmentary view, in perspective, of the jaws of the surgical instrument of FIG. 1 in the open position.
FIG. 6 is a fragmentary front view of a suture needle mounted on one of the jaws of the surgical instrument of FIG. 1.
FIG. 7 is a sectional view taken along line 7—7 in FIG. 6.
FIG. 8 is a fragmentary sectional view taken along line 8—8 in FIG. 1.

A surgical instrument 20 in accordance with the present invention, as illustrated in FIGS. 1 and 2, includes a pair of arms 22 and 24 pivotally connected at a joint 26. Arm 22 includes a jaw 28 and an elongate handle 30 with a finger loop 32. Similarly, arm 24 includes a jaw 34 and an elongate handle 36 with a finger loop 38. Jaws 28 and 34 are disposed distally of joint 26 and include pivotally opposed inner, tissue clamping surfaces 40 and 42 formed with longitudinally spaced ribs or teeth 44. Handles 30 and 36 are disposed proximally of joint 26 with finger loops 32 and 38 at terminal ends of the handles and a pair of mating protrusions 46 and 48 extending from handles 30 and 36 in opposed relation to lock arms 22 and 24 in various closed positions.

Arms 22 and 24, as thus far described, form a conventional apparatus for grasping and/or clamping anatomical tissue during surgical procedures and can have any desired configuration and be made of any suitable materials dependent upon the procedure to be performed and the desirability of being sterilizable for reuse or disposable for single patient use.

Figure 3:
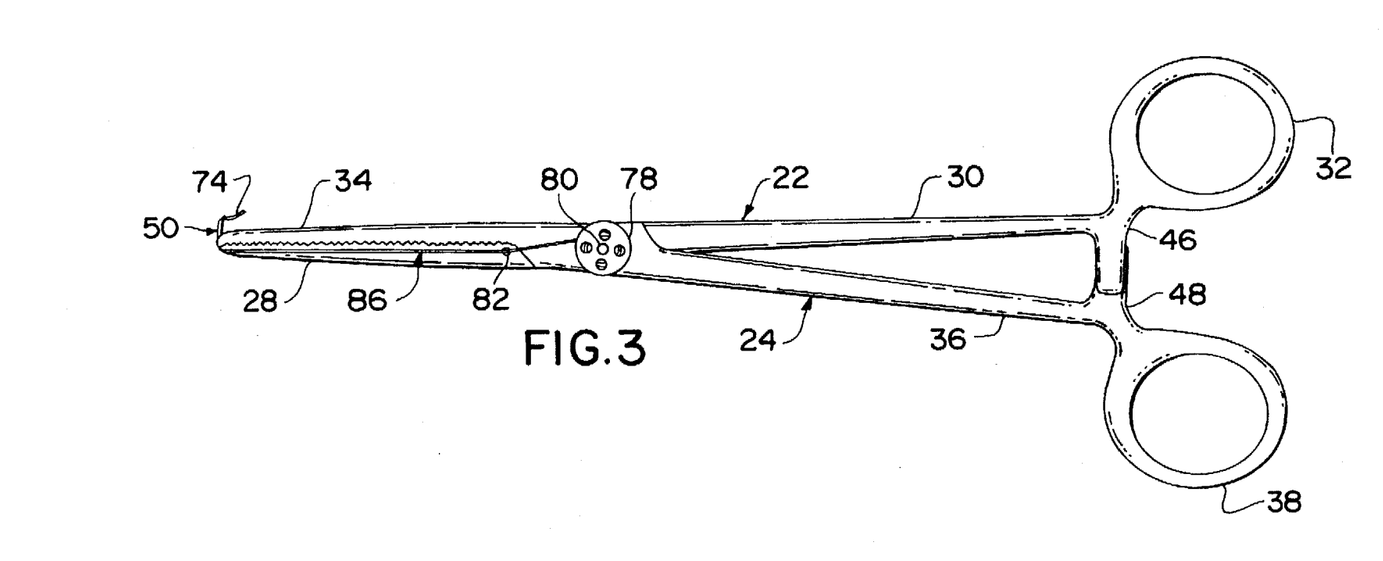
FIG. 3 is a side view, in elevation, of the surgical instrument of FIG. 1 in a closed position.
Figure 4:
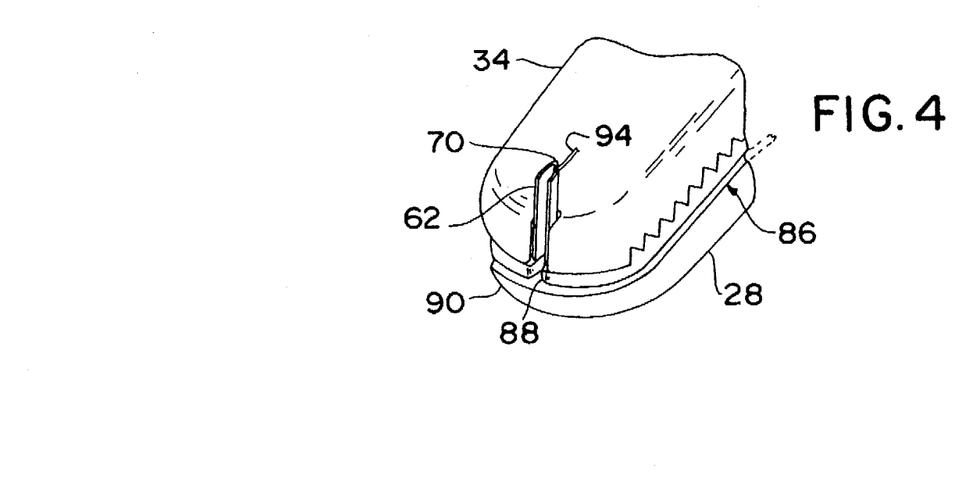
FIG. 4 is a fragmentary view, in perspective, of the jaws of the surgical instrument of FIG. 1 in the closed position.

In accordance with the present invention, a suture needle 50 is mounted on jaw 28 in opposed relation to an opening 52 formed through jaw 34, the opening being slotted or generally U-shaped with longitudinal edges 54 and 56 extending in parallel from a distal end or tip 58 of jaw 34 to a curved proximal edge 60 of the opening. As shown in FIGS. 3 and 4, the slotted opening 52 is aligned with needle 50 such that, when the jaws are closed, the needle will extend into the slotted opening.

Suture needle 50 includes a hollow, tubular body 62, as shown in FIGS. 5-7, extending substantially transversely from clamping surface 40 to a beveled end 64 where peripheral edges 66 and 68 of the needle converge to form a tip or point 70 for penetrating anatomical tissue to be sutured, a notch 72 being formed along peripheral edge 66 adjacent point 70 for attaching a length of suture material 74 to the needle. Tubular body 62 can be straight or curved and is preferably of circular cross-section, with an inner diameter $D_i$ of the tubular body being the same as or slightly larger than the diameter of the suture material 74 and a length of the body being such that, when the jaws are closed, the tip or point of the needle will protrude through the opening formed in the opposed jaw and extend beyond an outer surface of the opposed jaw. A slot 76 having a width W smaller than the diameter of suture material 74 is formed in tubular body 62 on a side of the tubular body opposite point 70 such that both the slotted opening 52 formed in jaw 34 and the slot 76 formed in needle 50 will face distally.

Referring again to FIGS. 1 and 2, suture material 74 is shown extending from a spool 78 rotatably mounted on a pin 80 secured to arm 24 adjacent junction 26, the spool being freely rotatable about the pin or ratcheted for controlled delivery of the suture material. The suture material extends distally from spool 78 into a funnel-shaped opening 82 formed in an outer surface 84 of jaw 28. The funnel-shaped opening communicates with a groove 86 formed along the outer surface of jaw 28, the groove 86 extending distally from the funnel-shaped opening to a bend 88 at the distal end or tip 90 of the jaw where the groove turns upward, looking at FIG. 5, to communicate with the interior of tubular needle body 62. An outermost edge of groove 86 intersects the outer surface 84 of jaw 28 to define an elongate slot 92, the groove being of circular cross-section like needle 50 with a diameter the same as or slightly larger than the diameter of the suture material and greater than the width of slot 92 so that suture material disposed within the groove will not fall from the groove through the slot without being urged laterally by application of force. Suture material 74 extends through the groove and the needle and is attached at the beveled end or tip of the needle via the notch 72.

In use, length of suture material 74 is fed from spool 78 into the funnel-shaped opening 82 formed in the outer surface of jaw 28 and is advanced through groove 86 into needle 50, for example, by manually rotating the spool or grasping the suture material near the spool with a forceps or gloved fingers, pushing the suture material forward, and releasing the suture material when the grasped portion nears the opening, the above steps being repeated until a distal end 94 of the suture material protrudes from the beveled end of the needle. The portion of the suture material protruding from the needle is then grasped, draped over notch 72 and pulled downward to cause the suture material to become wedged into the notch as shown in FIGS. 5 and 6.

Once suture material 74 has been attached to the needle 50, suturing instrument 20 can be grasped using a finger and thumb placed in finger loops 32 and 38 and moved to the anatomical tissue to be sutured. If closed, jaws 28 and 34 can be opened by pivoting handles 30 and 36 apart using the finger and thumb in finger loops 32 and 38.

Figure 9:
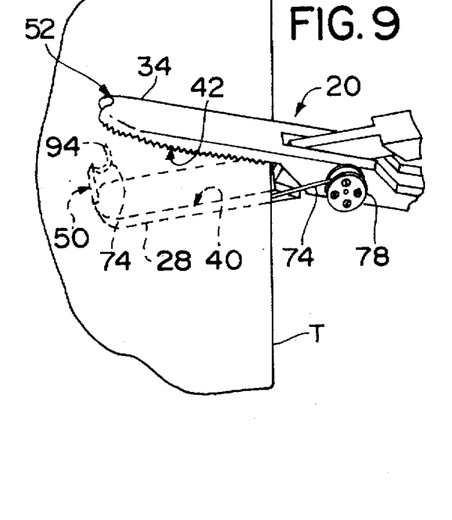
FIGS. 9–12 are fragmentary perspective views illustrating use of the surgical instrument of FIG. 1 for tissue clamping and suturing.
Figure 10:
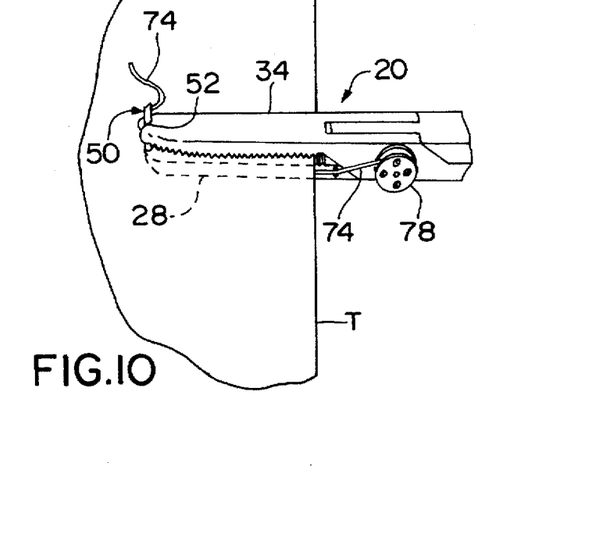

When anatomical tissue T is to be sutured (e.g., following dissection or division), jaws 28 and 34 are positioned on opposite sides of the tissue with needle 50 disposed immediately beyond the portion of the tissue to be clamped as shown in FIG. 9. Tissue T is then clamped between the jaws by squeezing the finger and thumb in finger loops 32 and 38 together to cause the tissue clamping surfaces 40 and 42 of the jaws to engage the tissue. At the same time, mating protrusions 46 and 48 engage one another to lock the jaws in the closed, clamping position and needle 50 is made to pass through the tissue and into slotted opening 52 carrying suture material 74 as shown in FIG. 10.

Figure 11:
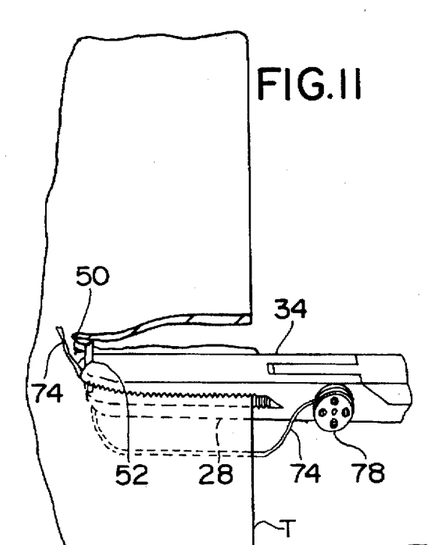

With tissue T clamped between jaws 28 and 34, a cut is made through the tissue on one side of the instrument adjacent the jaws, e.g., using a surgical scissors, and the portion of the suture material protruding from the needle is grasped and pulled away from notch 72 to release the suture material from the beveled end of the needle. Suture material 74 is also grasped near the spool and can be pulled from either grasped end, if necessary, to increase the length of suture material available for tieing-off or ligating the tissue. When a suitable length of suture material is obtained, the suture material is cut near the spool and opposite ends of the suture material are tugged sideways, in a transverse direction relative to longitudinal axes of the needle and groove, to force the suture material through slots 76 and 92 in the needle and jaw, respectively, such that the suture material will be released from the suturing instrument and disposed alongside jaws 28 and 34 on the side of the instrument opposite the cut as shown in FIG. 11.

Figure 12:
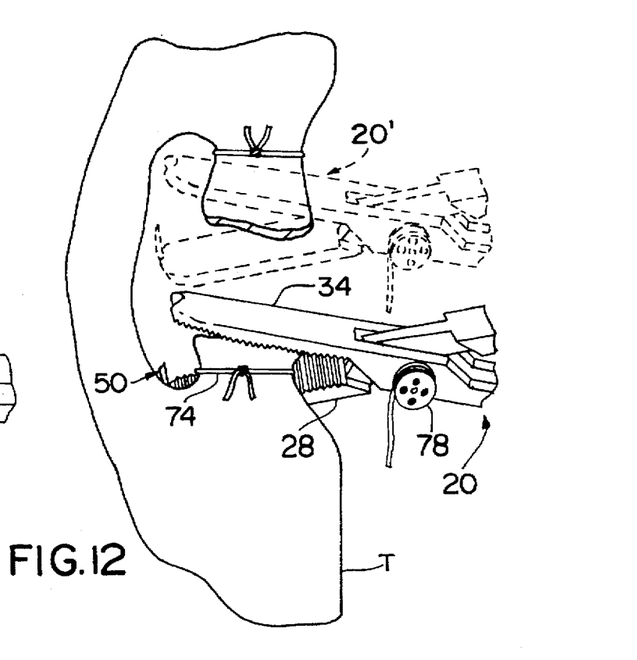

Once released from the surgical instrument, suture material 74 can be tied around tissue T immediately adjacent jaws 28 and 34 in the conventional manner while simultaneously opening the jaws to reduce the clamping pressure applied to the tissue as shown in FIG. 12. If it is desired to prevent bleeding from both sides of the cut, a similar procedure can be performed on the other side of the cut using a similar instrument 20' as shown by dotted lines in FIG. 12. Suturing instrument 20 is then moved away from the sutured tissue and is threaded in the manner described above for use at another location.

From the above, it will be appreciated that the surgical instrument 20 can be used anywhere in the body to form ligatures or ties around anatomical tissue using lengths of suture material carried by the instrument. The suturing instrument can, however, also be used to place stitches through anatomical tissue by positioning the tips of jaws 28 and 34 on opposite sides of the anatomical tissue to be sutured and closing the jaws in the manner described above to cause needle 50 carried by jaw 28 to penetrate through the anatomical tissue into the slotted opening formed in jaw 34. Suture material 74 carried at the beveled end of needle 50 is pulled through the anatomical tissue with the needle when the jaws are closed and can be released from the suturing instrument in the manner described above to be knotted in any conventional way or to be used in manipulating the anatomical tissue.

By mounting a suture needle on a jaw and attaching suture material to the needle mounted on the jaw, the surgical instrument of the present invention permits various types of sutures to be formed without the need of having to use multiple tissue clamping and needle holding instruments. Furthermore, since the needle is fixed at a predetermined location on the jaw opposite the slotted opening, it is possible to accurately position the needle adjacent anatomical tissue to be sutured without directly visually observing the needle. In the case of a needle being mounted at the tip of a jaw, positioning the tip of the jaw at a desired suturing location will also cause the needle to be properly positioned.

Under certain circumstances, it may be desirable to mount the suture needle in locations other than at the tip of the jaw. For example, in FIGS. 13 and 14, a modification of the surgical instrument is shown wherein the suture needle 50 is proximally spaced a short distance from the tip 90 of jaw 28. Slotted opening 52 in jaw 34 is aligned with needle 50 and elongated slightly such that the point of the needle will protrude from the slotted opening when the jaws are closed as shown in FIG. 14. Suture material 74 extends from groove 86 in the outer surface of jaw 28 to needle 50 through a groove extension 96 formed on the inner surface 40 of jaw 28 in alignment with a longitudinal axis of the jaw. Use of the surgical instrument 20 shown in FIGS. 13 and 14 is essentially as described above.

Any number of suture needles can be mounted on the jaw of the surgical instrument dependent upon the procedure to be performed. For example, in FIGS. 15 and 16, a modification of the surgical instrument 20 is shown wherein a pair of laterally spaced suture needles 50 are mounted at the tip of jaw 28 on opposite sides of a longitudinal cutting channel 98 formed along the inner surface 40 of the jaw in alignment with a longitudinal axis of the jaw. Each of the needles communicates with groove 86 formed along the periphery of the outer surface of jaw 28 so that separate lengths of suture material (not shown) supplied from opposite sides of the instrument can be carried by the needles in the manner described above for a single needle. A second cutting channel (shown by dotted lines at 98' in FIG. 15) can be formed in opposed relation to cutting channel 98 in jaw 34 so that, when jaws 28 and 34 are closed, a cutting member 100, such as a blade or scissors, can be movably disposed within the cutting channels and coupled with a rod or other advancing mechanism able to cause movement of the blade along the cutting channels.

Figures 13, 15:
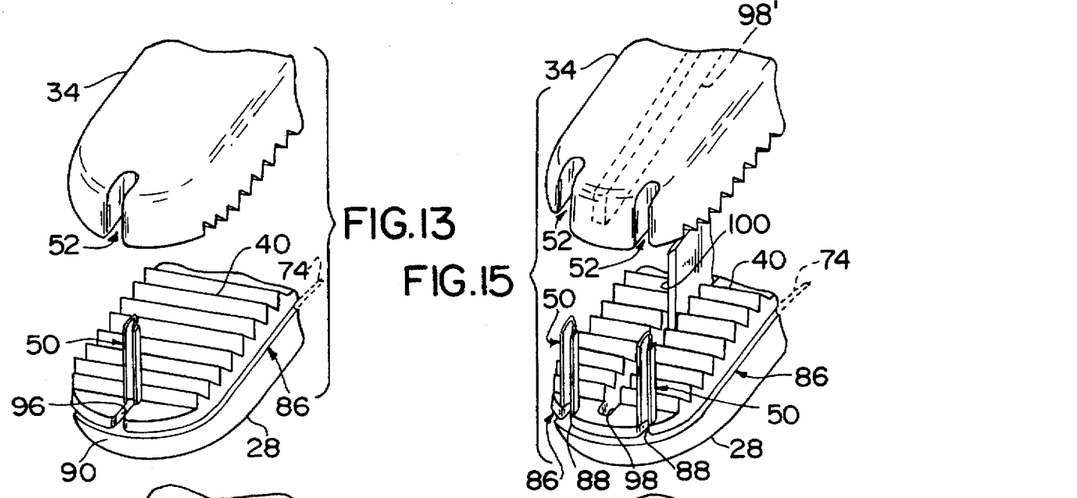
FIGS. 13 and 14 are fragmentary perspective views of a modification of the surgical instrument according to the present invention.
FIGS. 15 and 16 are fragmentary perspective views of another modification of the surgical instrument according to the present invention.
Figures 14, 16, 20:
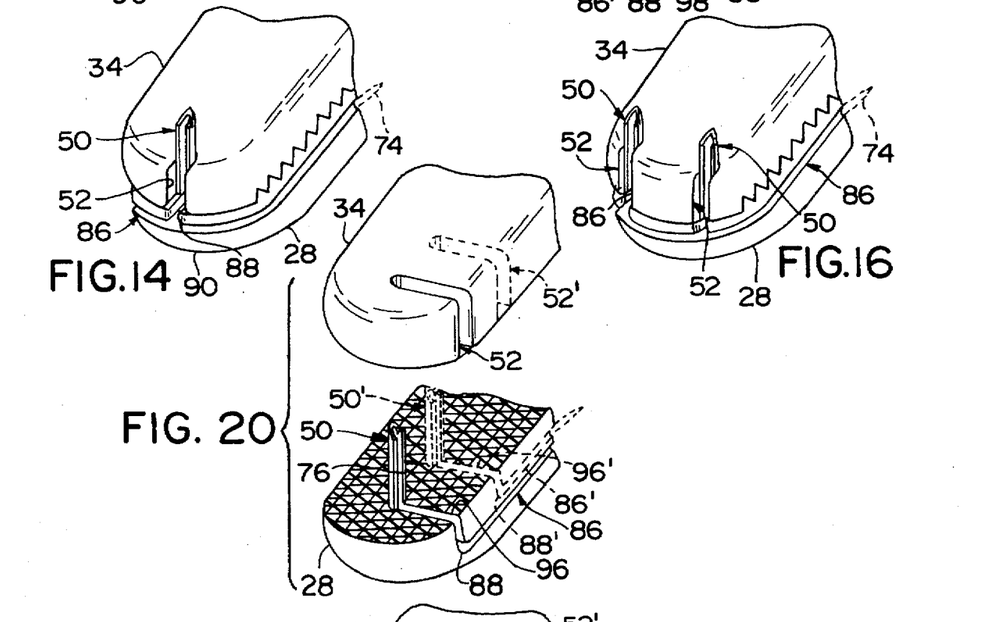
FIGS. 20 and 21 are fragmentary perspective views of still another modification of the surgical instrument according to the present invention.
Figure 17:
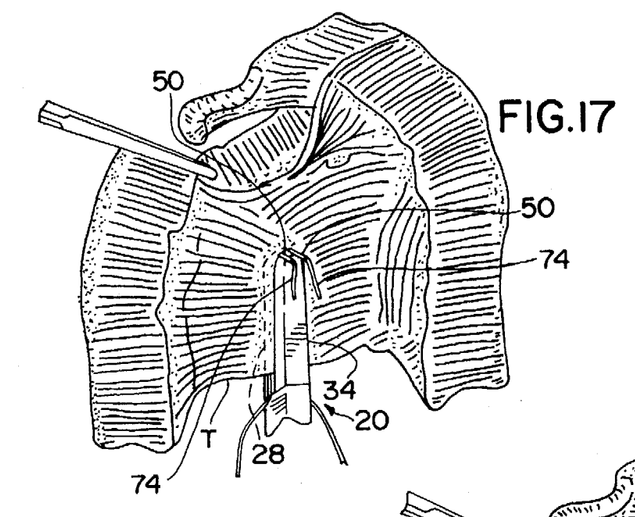
FIGS. 17–19 are fragmentary perspective views illustrating use of the surgical instrument of FIG. 15 for tissue clamping and suturing.
Figure 18:
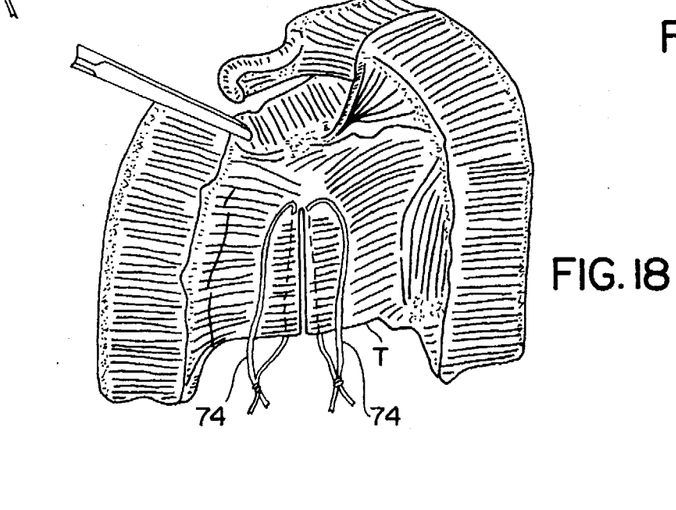
Figure 19:
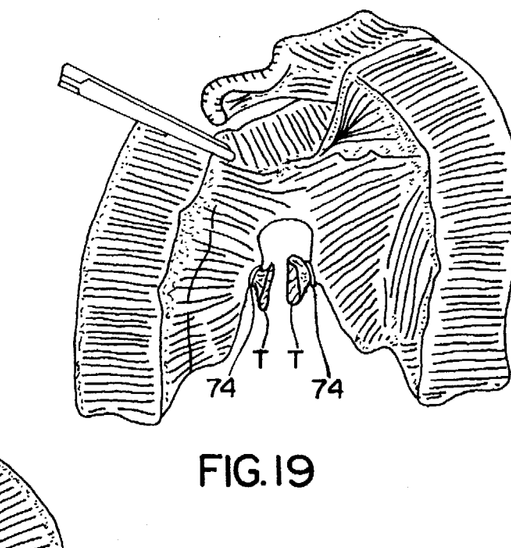

The surgical instrument shown in FIGS. 15 and 16 can be used to clamp and suture tissue in the same manner as described above. In addition, however, the surgical instrument of FIGS. 15 and 16 can be used to clamp, suture and cut tissue without the need of additional instruments. For example, in FIGS. 17–19, use of the surgical instrument for resecting a portion of the bowel is shown. In FIG. 17, jaws 28 and 34 have been placed on opposite sides of the bowel tissue T to be cut and have been clamped together by closing the jaws. At the same time, needles 50 have been made to penetrate through the tissue and to protrude from slotted openings 52. With tissue T held between the jaws, cutting member 100 is advanced distally along the cutting channels to cut the tissue clamped between the jaws. Before, during or after the cutting procedure, opposite ends of the suture material are grasped and tugged laterally relative to slots 76 to release the suture material from needles 50, the individual lengths of suture material thereby released being moved to opposite sides of the jaw as shown in FIG. 18 and tied in any conventional manner to rather the divided tissue as shown in FIG. 19. In addition to reducing the number of instruments needed to clamp, cut and suture tissue, it will be appreciated that the surgical instrument of FIG. 15 permits the suture material to be secured immediately adjacent the cut edge of the tissue thereby minimizing the size of the residual tissue stump or, in other words, the amount of tissue overhanging the suture.

Figure 21:
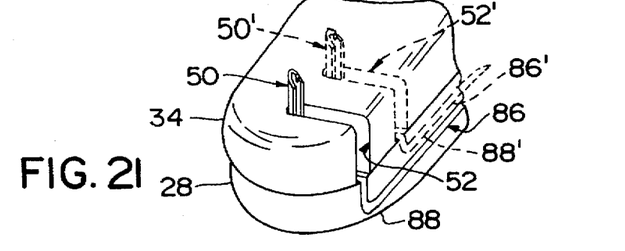

Another modification of the suturing instrument of the present invention is illustrated in FIGS. 20 and 21 wherein a suture needle 50 is proximally spaced from the tip of jaw 28 with slot 76 formed on a lateral side of the needle and slotted opening 52 formed in jaw 34 perpendicular to a longitudinal axis of the jaw. The slotted opening 52 extends from a lateral edge of the outer surface of the jaw in a transverse direction relative to a longitudinal axis of the jaw to be aligned with the needle such that, when the jaws are closed, the point of the needle will protrude from the slotted opening as shown in FIG. 21. Groove 86 formed in jaw 28 extends longitudinally along the outer surface of jaw 28 and turns upward, toward inner surface 40 of the jaw, at a bend 88 longitudinally aligned with slot 76 in the needle. The groove connects with a groove extension 96 at an edge of the inner surface, the groove extension extending transversely from the groove across the inner surface to communicate with the interior of needle 50.

In addition to the above, FIG. 20 illustrates a second needle, shown by dotted lines at 50', mounted on jaw 28 in opposed relation to a transverse slot, shown by dotted lines at 52', wherein the first and second needles 50 and 50' are longitudinally spaced in opposed relation to the slots 52 and 52' to facilitate certain suturing procedures. Also shown is a modification of inner surface 40 wherein, the surface is formed of a repeated pattern of diamond-shaped protrusions 44.

Figures 22, 23:
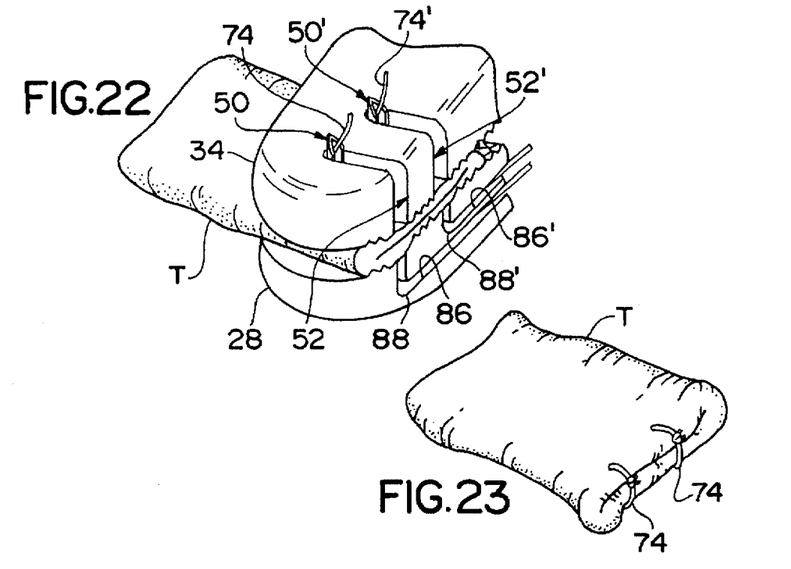
FIGS. 22 and 23 are fragmentary perspective views illustrating use of the surgical instrument of FIG. 20 for tissue clamping and suturing.

Use of the suturing instrument of FIGS. 20 and 21 in closing-off a tubular vessel or organ is illustrated in FIGS. 22 and 23 wherein jaws 28 and 34 are positioned on opposite sides of a vessel or organ T immediately adjacent a free end of the vessel or organ and are closed in the manner described above to clamp the tissue between the jaws and cause needles 50 and 50' to protrude from slotted openings 52 and 52'. Slots 76 and 76' and slotted openings 52 and 52' are oriented toward the free end of the tubular vessel or organ permitting suture material 74 and 74' to be drawn directly out of the needles 50 and 50' and tied around the free end as shown in FIG. 23 to form stitches closing the tubular vessel or organ.

Figures 24, 25, 26:
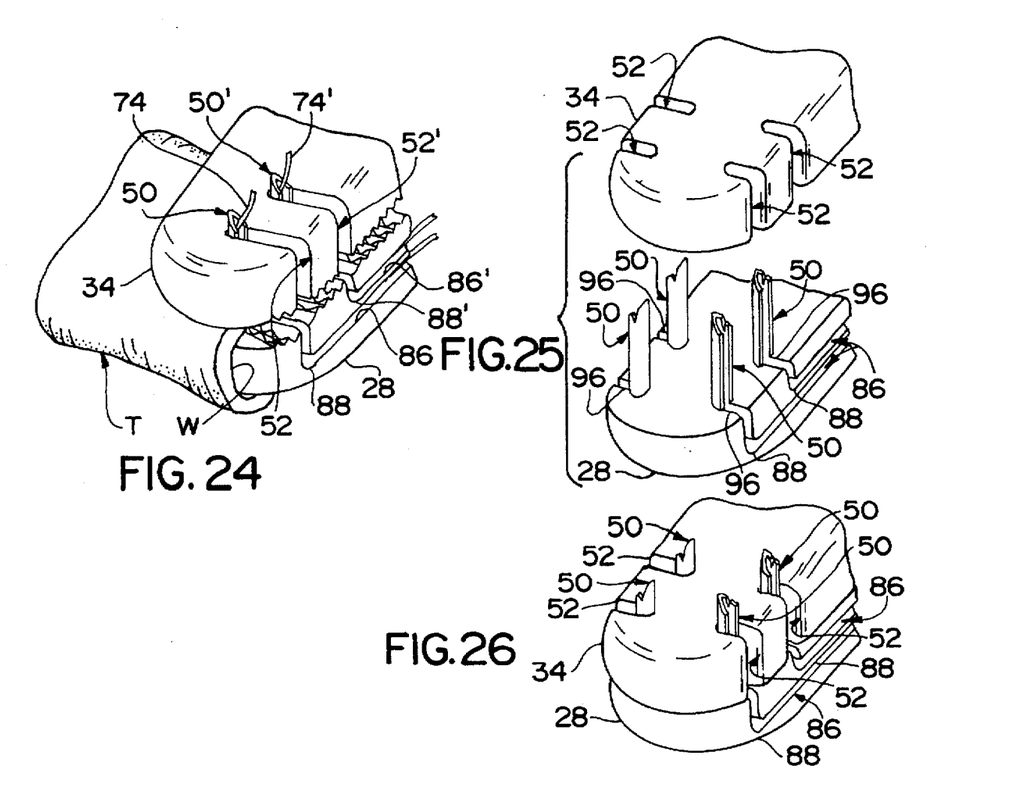
FIG. 24 is a fragmentary perspective view illustrating use of the surgical instrument of FIG. 20 to perform anastomosis.
FIGS. 25 and 26 are fragmentary perspective views of an additional modification of the surgical instrument according to the present invention.

The suturing instrument of FIG. 20 can also be used in the manner shown in FIG. 24 to place suture material in the walls of a tubular vessel or organ T by positioning jaw 28 inside the tubular vessel or organ with jaw 34 on the opposite side of a wall W of the vessel or organ and closing the jaws to cause needles 50 and 50' to penetrate through the tubular wall W. Lengths of suture material 74 and 74' are carried with the needles and, when passed through the wall W of the vessel T, the free ends of the suture material can, for example, be used in manipulating the tubular vessel or performing anastomosis.

It will be appreciated that the surgical instrument of FIG. 20 can also be used in a manner similar to that described above in connection with FIGS. 9–12 when it is desired to clamp anatomical tissue between the jaws, cut alongside the jaws and suture the tissue. Also, the surgical instruments of FIGS. 1, 13 and 15 can be used in a similar manner to that described above in connection with FIGS. 22–24.

The surgical instrument shown in FIGS. 25 and 26 is similar to those previously described but with two pairs of longitudinally spaced needles 50 mounted on jaw 28 in opposed relation to transverse openings 52 formed in jaw 34. The needles 50 are arranged in two laterally spaced rows with grooves 86 being formed on lateral sides of the outer surface of jaw 28 in communication with groove extensions 96 leading to each needle. Use of the modified surgical instrument shown in FIGS. 25 and 26 is similar to that described and shown for the instruments of FIGS. 1, 13, 15 and 20.

From the above, it will be appreciated that the surgical instrument of the present invention permits various types of sutures to be formed without the need of having to use multiple tissue clamping and needle holding instruments. By "sutures" is meant lengths of suture material secured to anatomical tissue as, for example, ligatures, ties or stitches. The lengths of suture material are attached to or carried by one or more suture needles mounted on at least one of two clamping jaws of the instrument, the suture material being removable therefrom when the jaws are closed so that the sutures can be set simultaneously with opening of the jaws if desired. While use of the instrument has been shown and described as including penetration of the anatomical tissue to be sutured, it will be appreciated that for certain types of procedures, the jaws of the instrument can also be positioned around the anatomical tissue with the point of the needle disposed beyond the tissue such that the needle will carry the suture material around the tissue to be sutured without penetrating through the tissue.

The needles can be straight or curved, rigid or flexible, and are preferably hollow and slotted with the point or tip of each needle being honed to a desired shape and configuration to form, for example, cutting points for hard to penetrate tissue such as skin and tendon, taper points for use in soft tissue such as intestine and peritoneum, or blunt points for use in suturing friable tissue. While it is preferred that the needles be hollow and slotted to reduce penetration resistance and the possibility of the suture material becoming snagged on other instruments or tissue, it is also possible to form the surgical instrument with solid needles and to attach lengths of suture material near the tips of the needles via slots or eyes, for example. The body or shaft of each needle can have any configuration in cross-section including, but not limited to, round, oval, flat and triangular cross-sectional configurations. Further, any of the needles described above can be coated to enhance smooth passage through the anatomical tissue being sutured. The gage or diameter and length of the body or shaft of each needle will vary depending upon the toughness of the tissue to be sutured and the depth of penetration desired. If an opening is formed in a jaw in opposed relation to a suture needle, the body of the needle should be sufficiently long to cause the point of the needle to protrude from the opening beyond an outer surface of the jaw when the jaws are clamped around anatomical tissue being sutured. The needles can be permanently affixed to a jaw to be sterilized of disposed of with the rest of the instrument or the needles can be removable for disposal or sterilization as desired. If removable, the needles can be coupled with the jaw using any suitable method such as, for example, friction fit, controlled release, threaded engagement or detents.

When an opening is formed in a jaw opposite a suture needle carried by an opposed jaw, the opening will preferably extend through the jaw and have a shape to receive the needle and communicate with an edge of the jaw. While elongated slots have been shown and described, other shapes can be used including polygonal and elliptical openings that communicate with an edge of the jaw.

The jaws of the surgical instrument can be straight, curved and/or angled and can have inner, tissue-engaging surfaces or faces for grasping and clamping anatomical tissue and/or objects such as needles. Any of the jaws shown or described herein can be formed with inner surfaces formed of repeated patterns of diamond-shaped protrusions, lateral and/or longitudinal ribs and/or other types of textured patterns suitable for clamping tissue to be sutured. One or both of the jaws can be formed with cutting members mounted on the jaws and/or with cutting channels for accommodating cutting members such as, for example, blades and scissors that are advanced along the channels and/or operated by opening and closing the jaws. Examples of cutting instruments that can be used with the surgical instrument of the present invention include any of the operating or cutting instruments shown in prior U.S. patent application Ser. No. 08/376,486, filed Jan. 20, 1995, the disclosure of which is incorporated herein by reference. The cutting channels can extend part way along the jaw to form stops or abutments limiting distal movement of the cutting members or can extend the complete length of a jaw to form openings or apertures at a distal end or tip of the jaw to allow passage of the cutting member beyond the tip of the jaw, e.g., to trim free ends of the suture material applied to tissue. When a cutting channel is formed between jaws of the instrument, one or more suture needles can be mounted along one side of the channel, on opposite sides of the channel (as shown in FIG. 15) or at the distal end of the channel. When the instrument is to be provided with cutting members, tissue positioned between the jaws can be cut simultaneously with clamping of the tissue (e.g., by use of scissors disposed within the cutting channels or cutting members mounted directly on the jaws) or the tissue can be cut subsequent to clamping (e.g., by advancing a blade along the cutting channels). The jaws can have any shape in cross-section when closed, including circular, elliptical, rectangular and polygonal configurations, and can have opposed arcuate or concave portions for holding tubular objects without compressing the objects.

Lengths of suture material are preferably attached near the point or tip of each needle to be easily grasped when extended through an opening in an opposed jaw. If the needles are hollow and slotted, the suture material is preferably passed through the needles to assure smooth penetration of anatomical tissue by the needle with minimum resistance and tissue trauma, the presence of the suture material at the open beveled end of the needle also helping to prevent coring of the tissue. If desired, the portion of the suture material overhanging the notch at the beveled end of the needle can be trimmed prior to penetrating anatomical tissue to further reduce tissue resistance. Upon penetrating through the tissue, the suture material can be advanced through the needle manually or by use of a feed mechanism to extend a suitable length for being grasped. Grooves can also be formed along the outer surfaces or sides of the jaws in communication with the hollow needles to serve as passages through which the suture material may extend and to prevent loose lengths of suture material from becoming snagged on other instruments or contaminating adjacent tissue structures or organs. By "outer surfaces" of the jaws are meant the surfaces not engaging anatomical tissue; however, grooves or groove extensions can also be formed in the inner, tissue-clamping surfaces of the jaws when necessary to communicate with needles spaced from edges of the jaws. A single groove can also be extended around the entire periphery of a jaw (as shown in FIGS. 4 and 5) and connected with a needle via an extension, if necessary, so that a length of suture material can be extended along either lateral side of the instrument into the needle depending upon which side of the instrument the suture is to be applied.

When the body of a hollow needle is slotted to permit removal of a length of suture material from within the needle, the slot can be straight or curved and of uniform or varying width as desired.

Any number of suture needles can be mounted on one or both jaws of the surgical instrument; and, while one needle or two needles in spaced relation have been shown mounted on a single jaw, it will be appreciated that greater than two needles can be mounted on a jaw in spaced relation, depending upon the length of the tissue to be sutured and the desired spacing between sutures. When multiple needles are mounted on a jaw of the instrument, the needles can be attached to free lengths of suture material, can be fed lengths of suture material from a single spool carrying multiple lengths of suture material, or can be fed from spools on opposite sides of the instrument such that lengths of suture material run along grooves on both sides of a jaw. Further, when spools are mounted on opposite sides of the instrument, lengths of suture material can be crossed at the tip of the jaw or elsewhere and then attached to respective needles so as to form cross-stitches or crossed-ligatures when tied or set. Whether fed from spools or provided as free lengths, the lengths of suture material can also be provided with knotting elements to assist in setting the sutures. Examples of knotting elements suitable for use with the present invention include those shown and described in prior U.S. patent applications Ser. No. 08/366,285, filed Dec. 29, 1994; Ser. No. 08/377,723, filed Jan. 25, 1995; Ser. No. 08/401,002, filed Mar. 9, 1995; and Ser. No. 08/531,153, entitled "Ligating Instrument With Multiple Loop Ligature Supply and Methods Therefor," filed Sep. 15, 1995, the disclosures of which are incorporated herein by reference.

The components of the surgical instrument of the present invention can be made of any suitable, medical grade materials to permit sterilization for re-use or for single patient use. The components can be made of multiple parts of various configurations and materials to reduce cost.

The features of the various embodiments described above can be combined in any manner desired dependent upon the operational requirements of the procedure to be performed and the complexity of the surgical instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
    a pair of pivotally connected arms, each arm defining a handle and a jaw;
    a hollow suture needle mounted on a first of said jaws, said hollow needle having a first open end mounted on said first jaw and a second open end adjacent a tissue penetrating point, said first and second open ends being connected by a slot formed in said hollow needle; and
    a length of suture material extending through said hollow needle;
    wherein said slot has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

2. A surgical instrument as recited in claim 1 wherein a groove is formed on an outer surface of said first jaw and a portion of said suture material is disposed within said groove.

3. A surgical instrument as recited in claim 2 wherein said groove communicates with said first open end of said hollow suture needle.

4. A surgical instrument as recited in claim 3 wherein said suture needle slot has a width smaller than a diameter of said length of suture material to prevent said suture material from falling out of said hollow suture needle.

5. A surgical instrument as recited in claim 4 wherein said groove decreases in width toward said outer surface of said first jaw to define an elongate slot along said outer surface of said first jaw having a width smaller than a diameter of said length of suture material to prevent said suture material from falling out of said groove.

6. A surgical instrument as recited in claim 5 wherein said hollow suture needle and said groove are of substantially circular cross-section.

7. A surgical instrument as recited in claim 2 and further comprising a spool disposed proximally of said groove, said length of suture material being dispensed from said spool.

8. A surgical instrument as recited in claim 1 wherein an opening is formed through a second of said jaws opposite said hollow suture needle, said opening extending inwardly from an edge of said second jaw to receive said hollow suture needle when said jaws are closed and to permit removal of said length of suture material from said closed jaws in a direction transverse to said needle longitudinal axis using said slot in said hollow suture needle and said opening in said second jaw.

9. A surgical instrument as recited in claim 8 wherein said needle has a length to cause said second open end of said needle to protrude from said second jaw opening when said jaws are closed.

10. A surgical instrument as recited in claim 9 wherein said opening is an elongate slotted opening communicating with an edge of said second jaw.

11. A surgical instrument as recited in claim 10 wherein said elongate opening extends longitudinally.

12. A surgical instrument as recited in claim 11 wherein said hollow suture needle is proximally spaced from a tip of said first jaw.

13. A surgical instrument comprising
    a pair of pivotally connected arms, each arm defining a handle and a jaw;
    a hollow suture needle mounted on a first of said jaws, said hollow needle having a first open end mounted on said first jaw and a second open end defining a tissue penetrating point, said first and second open ends being connected by a slot formed in said hollow needle; and
    a length of suture material extending through said hollow needle;
    wherein a notch is formed adjacent said point of said hollow suture needle and said length of suture material is held within said notch.

14. A surgical instrument as recited in claim 13 wherein said second open end is beveled to produce edges converging at said needle point and wherein said notch is formed along one of said bevel edges.

15. A surgical instrument as recited in claim 14 wherein said notch is V-shaped.

16. A surgical instrument comprising
    a pair of pivotally connected arms, each arm defining a handle and a jaw;
    a suture needle extending from a first of said jaws to a tissue penetrating point;
    a length of suture material extending along said suture needle and being coupled therewith to be removable therefrom in a transverse direction relative to a longitudinal axis of said needle; and
    an elongate slotted opening formed through a second of said jaws opposite said suture needle and communicating with an edge of said second jaw such that, when said jaws are closed, said suture needle will be received within said opening and said length of suture material will be removable from said closed jaws in a direction transverse to said needle longitudinal axis using said opening in said second jaw;

wherein said suture needle is proximally spaced from a tip of said first jaw and said elongate opening extends laterally from an edge of said second jaw transverse to a longitudinal axis of said second jaw.

17. A surgical instrument comprising a pair of pivotally connected arms, each arm defining a handle and a jaw, wherein said jaws define a tissue receiving space therebetween and wherein a cutting channel is formed in a first of said jaws parallel with a longitudinal axis of said first jaw;

a cutting member movably disposed along said longitudinal cutting channel and including a distal-facing cutting edge extending into said tissue receiving space between said jaws to cut anatomical tissue disposed between said jaws when said cutting member is longitudinally moved;

a suture needle extending from said first jaw to a tissue penetrating point; and a length of suture material carried by said suture needle.

18. A surgical instrument as recited in claim 17 wherein said suture needle is hollow and said suture material extends through said needle.

19. A surgical instrument as recited in claim 18 wherein a slot is formed in said hollow suture needle in communication with axially opposed ends of said needle.

20. A surgical instrument comprising a pair of pivotally connected arms, each arm defining a handle and a jaw, wherein a cutting channel is formed in a first of said jaws parallel with a longitudinal axis of said first jaw;

a cutting member movably disposed along said longitudinal cutting channel and having a cutting edge extending between said jaws to cut anatomical tissue disposed between said jaws when said cutting member is moved;

a suture needle extending from said first jaw to a tissue penetrating point; and a length of suture material carried by said suture needle;

wherein said suture needle is laterally offset from said longitudinal cutting channel.

21. A surgical instrument comprising a pair of pivotally connected arms, each arm defining a handle and a jaw;

a plurality of suture needles spaced longitudinally along a first of said jaws, each of said needles extending from said first jaw to a tissue penetrating point;

plural lengths of suture material, each of said lengths extending along a respective suture needle and coupled therewith to be removable therefrom in a transverse direction relative to a longitudinal axis of said suture needle; and opening means extending inwardly from an edge of a second of said jaws for receiving at least one of said suture needles when said jaws are closed and for permitting removal of a corresponding length of suture material from said at least one suture needle in a transverse direction relative to said needle longitudinal axis when said jaws are closed so that said length of suture material can be removed from said closed jaws and tied while simultaneously opening said jaws.

22. A surgical instrument as recited in claim 21 and further comprising a plurality of openings formed in said second jaw in opposed relation to said plurality of hollow needles, said openings each extending inwardly from an edge of said second jaw and being aligned with a hollow suture needle such that, when said jaws are closed, said hollow suture needles will be received within said elongate openings and said lengths of suture material can be removed from said closed jaws in a transverse direction relative to said longitudinal axes of said needles.

23. A surgical instrument comprising a pair of pivotally connected arms, each arm defining a handle and a jaw;

a plurality of suture needles spaced longitudinally along a first of said jaws, each of said needles extending from said first jaw to a tissue penetrating point;

plural lengths of suture material, each of said lengths extending along a respective suture needle and being removable therefrom in a transverse direction relative to a longitudinal axis of said suture needle; and an opening extending inwardly from an edge of a second of said jaws to receive at least one of said suture needles when said jaws are closed and to permit removal of a corresponding length of suture material from said at least one suture needle in a transverse direction relative to said needle longitudinal axis when said jaws are closed so that said length of suture material can be removed from said closed jaws and tied while simultaneously opening said jaws;

wherein each of said suture needles is hollow and axially opposed ends of each hollow suture needle are open and connected by a slot formed in said hollow suture needle, each length of suture material extending through one of said hollow suture needles;

wherein each of said slots has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

24. A surgical instrument as recited in claim 23 wherein a plurality of grooves are formed in an outer surface of said first jaw to hold said lengths of suture material.

25. A surgical instrument comprising a pair of pivotally connected arms, each arm defining a handle and a jaw;

a plurality of suture needles spaced laterally across a first of said jaws, each of said needles extending from said first jaw to a tissue penetrating point;

plural lengths of suture material, each of said lengths extending along a respective suture needle and coupled therewith to be removable therefrom in a lateral direction relative to a longitudinal axis of said suture needle; and opening means extending inwardly from an edge of a second of said jaws for receiving at least one of said suture needles when said jaws are closed and for permitting removal of a corresponding length of suture material from said at least one suture needle in a transverse direction relative to said needle longitudinal axis when said jaws are closed so that said length of suture material can be removed from said closed jaws and tied while simultaneously opening said jaws.

26. A surgical instrument as recited in claim 25 wherein said opening means includes a plurality of openings formed in said second jaw in opposed relation to said plurality of suture needles, said openings each extending inwardly from an edge of said second jaw and being aligned with a suture needle such that, when said jaws are closed, said suture needles will be received within said openings and said lengths of suture material can be removed from said closed jaws in a transverse direction relative to said longitudinal axes of said needles.

27. A surgical instrument comprising a pair of pivotally connected arms, each arm defining a handle and a jaw;

a plurality of suture needles spaced laterally across a first of said jaws, each of said needles extending from said first jaw to a tissue penetrating point;

plural lengths of suture material, each of said lengths extending along a respective suture needle and being removable therefrom in a lateral direction relative to a longitudinal axis of said suture needle; and an opening extending inwardly from an edge of a second of said jaws to receive at least one of said suture needles when said jaws are closed and to permit removal of a corresponding length of suture material from said at least one suture needle in a transverse direction relative to said needle longitudinal axis when said jaws are closed so that said length of suture material can be removed from said closed jaws and tied while simultaneously opening said jaws;

wherein each of said suture needles is hollow and axially opposed ends of each hollow suture needle are open and connected by a slot formed in said hollow suture needle, each length of suture material extending through one of said hollow suture needles;

wherein each of said slots has a width preventing said length of suture material from falling out of said hollow suture needle in a direction transverse to a longitudinal axis of said needle while permitting said length of suture material to be removed from said hollow suture needle when urged in a direction transverse to said needle longitudinal axis.

28. A surgical instrument as recited in claim 27 wherein a plurality of grooves are formed in an outer surface of said first jaw to hold said lengths of suture material.

29. A surgical instrument comprising a pair of pivotally connected arms, each arm defining a handle and a jaw;

a plurality of suture needles spaced laterally across a first of said jaws, each of said needles extending from said first jaw to a tissue penetrating point; and plural lengths of suture material, each of said lengths being carried by one of said suture needles;

wherein a cutting channel is formed in said first jaw parallel with a longitudinal axis of said first jaw between laterally spaced suture needles and further comprising a cutting member movably disposed along said cutting channel and having a cutting edge extending between said jaws to cut anatomical tissue disposed between said jaws.

30. A surgical instrument comprising a pair of pivotally connected arms, each arm defining a handle and a jaw;

a hollow suture needle mounted on a first of said jaws, said hollow needle having a first open end mounted on said first jaw and a second open end with a peripheral edge defining a tissue penetrating point, said first and second open ends being connected by a slot formed in said hollow needle; and a length of suture material extending through said hollow needle, said length of suture material being of a size to be removable from said hollow suture needle in a direction transverse to a longitudinal axis of said needle using said slot.

31. A surgical instrument comprising a pair of pivotally connected arms, each arm defining a handle and a jaw;

a substantially straight, hollow suture needle mounted on a first of said jaws, said hollow needle having a first open end mounted on said first jaw and a second open end adjacent a tissue penetrating point, said first and second open ends being connected by a slot formed in said hollow needle; and a length of suture material extending through said hollow needle, said length of suture material being of a size to be removable from said hollow suture needle in a direction transverse to a longitudinal axis of said needle using said slot.

32. A surgical instrument comprising a pair of pivotally connected arms, each arm defining a handle and a jaw;

a suture needle extending from a first of said jaws toward a second of said jaws and terminating at a tissue penetrating point;

a groove formed on an outer surface of said first jaw; and a length of suture material extending through said groove and along said suture needle to be disposed adjacent said tissue penetrating point, said groove decreasing in width toward said outer surface of said first jaw to define a slot having a width preventing said length of suture material from falling out of said groove.

33. A surgical instrument as recited in claim 32 wherein said width of said slot defined by said groove is such that said length of suture material can be removed from said groove by urging said suture material laterally through said slot by application of force.

* * * * *